United States Patent [19]

Bernhagen et al.

[11] Patent Number: 4,515,986

[45] Date of Patent: May 7, 1985

[54] PROCESS FOR PREPARING 3-DIMETHYLAMINO-2,2-DIMETHYL-PROPANAL

[75] Inventors: Wolfgang Bernhagen, Mülheim; Volker Falk, Oberhausen; Helmut Springer, Oberhausen; Jürgen Weber, Oberhausen; Ernst Wiebus, Oberhausen; Claus Kniep, Oberhausen, all of Fed. Rep. of Germany

[73] Assignee: Ruhrchemie Aktiengesellschaft, Oberhausen, Fed. Rep. of Germany

[21] Appl. No.: 294,114

[22] Filed: Aug. 19, 1981

[30] Foreign Application Priority Data

Aug. 19, 1980 [DE] Fed. Rep. of Germany ....... 3031248

[51] Int. Cl.$^3$ .................... C07C 85/00; C07C 85/18

[52] U.S. Cl. .................... 564/471; 564/502

[58] Field of Search ................ 564/471, 502

[56] References Cited

U.S. PATENT DOCUMENTS

| | | | |
|---|---|---|---|
| 1,824,676 | 9/1931 | Mannich | 564/471 |
| 2,580,494 | 1/1952 | Wilder et al. | 564/471 X |
| 4,148,824 | 4/1979 | Hoffmann et al. | 564/471 |

*Primary Examiner*—Paul F. Shaver
*Attorney, Agent, or Firm*—Sprung Horn Kramer & Woods

[57] ABSTRACT

An improved process for preparing 3-dimethylamino-2,2-dimethylpropanal from isobutyraldehyde, dimethylamine and a source of formaldehyde is disclosed wherein the process is carried out at a pH value of 9 to 11.

11 Claims, No Drawings

PROCESS FOR PREPARING 3-DIMETHYLAMINO-2,2-DIMETHYLPROPANAL

BACKGROUND OF THE INVENTION

1. Field of the Invention

The present invention relates to a process for preparing 3-dimethylamino-2,2-dimethylpropanal from isobutyraldehyde, formaldehyde and dimethylamine.

2. Discussion of Prior Art

Aminoaldehydes which are derived from the neopentyl structure (i.e. 2,2-dimethylpropyl structure) are of great interest as intermediates for the preparation of pharmaceuticals, plant growth hormones, fungicides, herbicides and flotation auxiliaries. Aminoaldehydes which have a tertiary amino group in the 3-position in addition to the central branching of the carbon chain are of particular importance. These compounds are used, for example, to prepare 3-aminopyridine derivatives, 1,2-dihalopyridazines, benzo-1,3-dioxans, substituted imidazoles and amidines.

It is known to prepare alkyl aminoaldehydes by condensation of CH-acid compounds with formaldehyde and ammonia or amines (Mannich et al in Reports 65, 387 (1932)). This conversion, which can be classified as a special case in the framework of the broad aminomethylation type of reaction, is described as a Mannich reaction.

To form 3-dimethylamino-2,2-dimethylpropanal by the Mannich reaction, one starts from isobutyraldehyde, paraformaldehyde and dimethylamine hydrochloride (Mannich, loc. cit.). An essential feature of this procedure is the presence of an acid, which is added to the reaction medium either as such or in the form of the amine salt. The condensation thus proceeds in an acid medium.

The necessity of operating at pH values below 7 has considerable disadvantages, which lead to serious difficulties in producing the compounds on a technical scale. In addition to the Mannich reaction, a trimerization of isobutyraldehyde to 2,4,6-triisopropyl-1,3,5-trioxane in fact also takes place in acid media, and the yield of the desired aminoaldehyde is considerably reduced. If hydrochloric acid is employed, it is essential to use halogen-resistant reactors.

Moreover, the Mannich base is formed as a salt, from which the aminoaldehyde has to be obtained via a very complicated and costly working-up procedure, which to some extent involves environmentally harmful procedures. The object, therefore, existed of developing a process which avoids the indicated disadvantages and also enables 3-dimethylamino-2,2-dimethylpropanal to be produced in a simple manner on a technical scale.

SUMMARY OF THE INVENTION

It has now surprisingly been found that 3-dimethylamino-2,2-dimethylpropanal can be obtained from isobutyraldehyde, dimethylamine and formaldehyde or a source of formaldehyde at 80° to 120° C. if the conversion is carried out at pH values of 9 to 11.

The starting substances are used in stoichiometric molar ratios, though an excess of dimethylamine is not damaging. Isobutyraldehyde and dimethylamine are used in their commercially available form. Formaldehyde may be reacted in the gaseous form, as an aqueous solution, or as a polymer such as paraformaldehyde or triethoxymethylene. The presence of a solvent for the starting substances and/or the reaction product is not essential, and the presence of water—when using an aqueous formaldehyde solution—does not disturb the reaction.

The pH range characteristics of the process according to the invention is established in the reaction medium on account of the presence of the amine. It is particularly advantageous to operate at pH values of 9 to 11. In order to obtain such pH values, excess amine must, if necessary, be employed.

The conversion can be carried out batchwise in a pressurized vessel in which isobutyraldehyde and formaldehyde are first placed and are then mixed with the dimethylamine to 80° to 120° C., a pressure of 1.5 to 4 bars being established. The reaction time is 1 to 6 hours, depending on the temperature employed. In the continuous method of reaction the starting substances are fed separately to a flow tube and left to react at a residence time of 0.5 to 3 hours.

The reaction mixture is worked up by distillation. When using aqueous formaldehyde solution, an aqueous phase and an organic phase are formed, which are separated from one another. The 3-dimethylamino-2,2-dimethylpropanal can subsequently be isolated from the organic phase.

The invention is described in more detail in the following examples:

EXAMPLE 1

720 grams (10 mols) of isobutyraldehyde and 1000 grams of aqueous, 30% formaldehyde solution (10 mols) are placed in a 5 l stirred autoclave and mixed with 450 grams of gaseous dimethylamine (10 mols). The mixture, which has a pH value of 11, is heated to 100° C. while stirring and left to stand for 5 hours at this temperature. An internal pressure of 1.8 to 2.5 bars is produced. After the end of the reaction time, the reaction mixture is allowed to cool and the product is removed from the autoclave. 1340 grams of an organic phase and 830 grams of an aqueous phase are formed, and are separated. By vacuum distillation of the organic phase in a column having 24 trays, 946 grams of 3-dimethylamino-2,2-dimethypropanal is formed in a purity of more than 98%, corresponding to a yield of about 71.8%, and having the following characteristics:

| Density | $d\frac{20}{4}$ | 0.852 |
| --- | --- | --- |
| Refractive index: | $n\frac{20}{D}$ | 1.4231 |
| Carbonyl number: | | 440 mg KOH/g |
| Boiling point: | | 98° C./150 mm Hg |

EXAMPLE 2

600 grams of isobutyraldehyde, 833 grams of aqueous 30% formaldehyde solution and 375 grams of dimethylamine are introduced per hour via separate lines into the base of a vertically arranged flow tube. A pressure of 20 to 25 bars is maintained with nitrogen. A reaction product of roughly the following composition is obtained at a reaction temperature of 100° C. and an average residence time of about 1 hour, at the head of the reactor:

| First runnings | 4.0% by weight |
| --- | --- |

| | |
|---|---|
| Isobutyraldehyde | 0.9% by weight |
| 3-dimethylamino-2,2-dimethylpropanal | 49.9% by weight |
| Higher boiling fractions | 4.7% by weight |
| Water | 40.5% by weight |

The selectivity of the conversion to 3-dimethylamino-2,2-dimethylpropanal is accordingly about 84% of theory.

By subsequent distillation, as in Example 1, a product having a purity of about 98% is obtained.

What is claimed is:

1. In a process for preparing 3-dimethylamino-2,2-dimethylpropanal from isobutyraldehyde, dimethylamine and a source of formaldehyde at 80° to 120° C., the improvement wherein the reaction is carried out at a pH-value of 9 to 11.

2. A process according to claim 1, wherein the process is carried out batchwise in a pressurized vessel.

3. A process according to claim 1, wherein the process is carried out continuously by feeding the starting substances into a flow tube and allowing them to react therein over a period of time of 0.5 to 3 hours.

4. A process according to claim 1, wherein the formaldehyde is supplied in the form of a gaseous formaldehyde.

5. A process according to claim 1, wherein the formaldehyde is supplied in the form of an aqueous solution.

6. A process according to claim 1, wherein the formaldehyde is supplied in the form of a polymer.

7. A process according to claim 6, wherein said polymer is paraformaldehyde or triethoxymethylene.

8. A process according to claim 1, wherein the process is carried out in the presence of water.

9. A process according to claim 1, wherein the process is carried out in the absence of a solvent.

10. A process according to claim 1, wherein the reaction is carried out in 1 to 6 hours.

11. A process according to claim 1, wherein said dimethylamine is gaseous dimethylamine.

* * * * *